US012778912B2

(12) United States Patent
Matsumoto et al.

(10) Patent No.: US 12,778,912 B2
(45) Date of Patent: Nov. 3, 2026

(54) PHARMACEUTICAL COMPOSITION

(71) Applicant: TANABE PHARMA CORPORATION, Osaka (JP)

(72) Inventors: Hideaki Matsumoto, Osaka (JP); Shogo Yoshizawa, Osaka (JP); Daisuke Wakebayashi, Osaka (JP)

(73) Assignee: TANABE PHARMA CORPORATION, Osaka (JP)

( * ) Notice: Subject to any disclaimer, the term of this patent is extended or adjusted under 35 U.S.C. 154(b) by 768 days.

(21) Appl. No.: 17/911,329

(22) PCT Filed: Mar. 30, 2021

(86) PCT No.: PCT/JP2021/013580
§ 371 (c)(1),
(2) Date: Sep. 13, 2022

(87) PCT Pub. No.: WO2021/200975
PCT Pub. Date: Oct. 7, 2021

(65) Prior Publication Data

US 2023/0115921 A1 Apr. 13, 2023

(30) Foreign Application Priority Data

Mar. 31, 2020 (JP) ................................ 2020-063606

(51) Int. Cl.
*A61K 31/138* (2006.01)
*A61K 9/48* (2006.01)

(52) U.S. Cl.
CPC .......... *A61K 31/138* (2013.01); *A61K 9/4825* (2013.01); *A61K 9/485* (2013.01); *A61K 9/4858* (2013.01)

(58) Field of Classification Search
CPC .............. A61P 3/10; A61P 11/02; A61P 17/00
See application file for complete search history.

(56) References Cited

U.S. PATENT DOCUMENTS

| | | | |
|---|---|---|---|
| 2009/0137530 | A1* | 5/2009 | Masatoshi et al. |
| 2017/0291917 | A1 | 10/2017 | Fyfe et al. |
| 2019/0246312 | A1* | 8/2019 | Jones et al. |

FOREIGN PATENT DOCUMENTS

| | | | |
|---|---|---|---|
| CN | 110662755 | A | 1/2020 |
| JP | 2002-284679 | A | 10/2002 |
| JP | 2002284679 | * | 10/2002 |
| JP | 2016-155777 | A | 9/2016 |
| JP | 2016155777 | * | 9/2016 |
| WO | 2007/069712 | A1 | 6/2007 |
| WO | WO 2018/217699 | A1 | 11/2018 |
| WO | WO 2019/118778 | A1 | 6/2026 |

OTHER PUBLICATIONS

International Search Report for PCT/JP2021/013580(PCT/ISA/210) mailed on Jun. 1, 2021.
Extended Europea Search Report for European Application No. 21781077.9, dated Sep. 14, 2023.

* cited by examiner

*Primary Examiner* — Robert A Wax
*Assistant Examiner* — Kimberly Barber
(74) *Attorney, Agent, or Firm* — Birch, Stewart, Kolasch & Birch, LLP

(57) ABSTRACT

A pharmaceutical composition of 2-amino-2-[2-(4-heptyloxy-3-trifluoromethylphenyl)ethyl]propane-1,3-diol or a salt thereof is provided. The composition is superior in storage stability and can suppress production of related substances.

An excipient selected from dibasic calcium phosphate, calcium dihydrogen phosphate, dibasic sodium phosphate, and sodium dihydrogen phosphate is used.

15 Claims, No Drawings

PHARMACEUTICAL COMPOSITION

TECHNICAL FIELD

The present invention relates to a pharmaceutical composition comprising 2-amino-2-[2-(4-heptyloxy-3-trifluoromethylphenyl)ethyl]propane-1,3-diol or a salt thereof.

BACKGROUND ART

Patent document 1 discloses 2-amino-2-[2-(4-heptyloxy-3-trifluoromethylphenyl)ethyl]propane-1,3-diol hydrochloride useful as a medicament superior in an immunosuppressive action, a rejection suppressive action, and the like.

DOCUMENT LIST

Patent Document

Patent document 1: International publication No. WO 2007/069712

SUMMARY OF INVENTION

An object of the present invention is to provide a pharmaceutical composition comprising 2-amino-2-[2-(4-heptyloxy-3-trifluoromethylphenyl)ethyl]propane-1,3-diol or a pharmaceutically acceptable salt thereof. The composition is superior in storage stability and can suppress production of related substances.

Solution to Problem

The present inventors have conducted intensive studies in an attempt to solve the aforementioned problem and found that the production of related substances can be suppressed by using (b) an excipient such as dibasic calcium phosphate, calcium dihydrogen phosphate, dibasic sodium phosphate, or sodium dihydrogen phosphate, as a component of a pharmaceutical composition comprising 2-amino-2-[2-(4-heptyloxy trifluoromethylphenyl)ethyl]propane-1,3-diol or a salt thereof, which resulted in the completion of the present invention.

2-Amino-2-[2-(4-heptyloxy trifluoromethylphenyl)ethyl]propane-1,3-diol or a pharmaceutically acceptable salt thereof is disclosed in, for example, U.S. Pat. No. 8,809,314, the contents of which are incorporated in full herein for reference.

Accordingly, the present invention provides the following.

[1] A pharmaceutical composition comprising (a) 2-amino-2-[2-(4-heptyloxy-3-trifluoromethylphenyl)ethyl]propane-1,3-diol or a pharmaceutically acceptable salt thereof, and (b) one or more excipients selected from dibasic calcium phosphate, calcium dihydrogen phosphate, dibasic sodium phosphate, and sodium dihydrogen phosphate.

[2] The pharmaceutical composition of the above-mentioned [1], further comprising (c) sugar alcohol.

[3] The pharmaceutical composition of the above-mentioned [2], wherein the component (c) sugar alcohol is mannitol or sorbitol.

[4] The pharmaceutical composition of the above-mentioned [3], wherein the component (c) sugar alcohol is mannitol.

[5] The pharmaceutical composition of any of the above-mentioned [2] to [4], wherein a weight ratio of the component (b) excipient and the component (c) sugar alcohol (component (b):component (c)) is 10:90 to 75:25.

[6] The pharmaceutical composition of any of the above-mentioned [1] to [5], wherein the component (b) excipient is anhydrous dibasic calcium phosphate.

[7] The pharmaceutical composition of any of the above-mentioned [1] to [6], further comprising talc.

[8] The pharmaceutical composition of any of the above-mentioned [1] to [7], wherein the composition is filled in a gelatin capsule.

[9] The pharmaceutical composition of any of the above-mentioned [1] to [8], wherein the component (a) 2-amino-2-[2-(4-heptyloxy-3-trifluoromethylphenyl)ethyl]propane-1,3-diol or a pharmaceutically acceptable salt thereof is 2-amino-2-[2-(4-heptyloxy-3-trifluoromethylphenyl)ethyl]propane-1,3-diol hydrochloride.

[10] The pharmaceutical composition of any of the above-mentioned [1] to [9], wherein a weight ratio of the component (a) 2-amino-2-[2-(4-heptyloxy-3-trifluoromethylphenyl)ethyl]propane-1,3-diol or a pharmaceutically acceptable salt thereof and a total amount of the component (b) excipient and the component (c) sugar alcohol (component (a):total amount of component (b) and component (c)) is 1:999 to 20:980.

[11] The pharmaceutical composition of any of the above-mentioned [1] to [10], wherein a content of the component (a) 2-amino-2-[2-(4-heptyloxy-3-trifluoromethylphenyl)ethyl]propane-1,3-diol or a pharmaceutically acceptable salt thereof is an amount of 2-amino-2-[2-(4-heptyloxy-3-trifluoromethylphenyl)ethyl]propane-1,3-diol, and is 0.1 to 0.4 mg with respect to 60 mg of the pharmaceutical composition excluding a weight of a capsule when the composition is filled in the capsule.

[12] The pharmaceutical composition of any of the above-mentioned [1] to [11], wherein the pharmaceutical composition is a solid pharmaceutical composition.

[13] A pharmaceutical composition comprising (a) 2-amino-2-[2-(4-heptyloxy-3-trifluoromethylphenyl)ethyl]propane-1,3-diol or a pharmaceutically acceptable salt thereof, and (b') excipient, wherein the component (b') excipient is an excipient wherein a total peak area of related substances of the component (a) (that is, total value of the peak areas of the related substances) is less than 0.3% with respect to the total value of a peak area of the component (a) and the total peak area of the related substances of the component (a), in a peak area detected by HPLC (high performance liquid chromatography) of a mixture of the component (a) and the component (b') mixed such that a weight ratio thereof (component (a):component (b')) is 1:999 and stored open at 40° C., 75% RH for 4 weeks.

[14] The pharmaceutical composition of the above-mentioned [13], wherein the total peak area of the related substances of the component (a) is 0.2% or less with respect to the total value of the peak area of the component (a) and the total peak area of the related substances of the component (a).

Advantageous Effects of Invention

The pharmaceutical composition of the present invention shows superior storage stability by suppressing the production of related substances of 2-amino-2-[2-(4-heptyloxy-3-trifluoromethylphenyl)ethyl]propane-1,3-diol or a pharmaceutically acceptable salt thereof. Therefore, a pharmaceutical composition having sufficient storage stability as a medicament can be provided.

DESCRIPTION OF EMBODIMENTS

The present invention provides a pharmaceutical composition containing (a) 2-amino-2-[2-(4-heptyloxy-3-trifluoromethylphenyl)ethyl]propane-1,3-diol or a pharmaceutically acceptable salt thereof (hereinafter sometimes to be referred to as "main drug"), and (b) one or more excipients selected from dibasic calcium phosphate, calcium dihydrogen phosphate, dibasic sodium phosphate, and sodium dihydrogen phosphate. Particularly, the present invention provides a pharmaceutical composition further containing (c) sugar alcohol.

The pharmaceutically acceptable salt of the main drug component (a) is generally a pharmaceutically acceptable acid addition salt. The acid addition salt is not particularly limited and, for example, inorganic acid salt, organic acid salt, alkali metal salt, alkaline earth metal salt, and the like can be mentioned. Among these, hydrochloride is preferred.

The main drug component (a) is preferably 2-amino-2-[2-(4-heptyloxy-3-trifluoromethylphenyl)ethyl]propane-1,3-diol hydrochloride.

The amount of the main drug component (a) is an amount of 2-amino-2-[2-(4-heptyloxy-3-trifluoromethylphenyl)ethyl]propane-1,3-diol, and it is preferably contained in an amount of 0.05-1.0 part(s) by weight, more preferably 0.1-0.4 parts by weight, with respect to 60 parts by weight of the pharmaceutical composition (when filled in a capsule, 60 parts by weight of the pharmaceutical composition excluding the weight of the capsule). When the component (a) is less than 0.1 parts by weight with respect to 60 parts by weight of the pharmaceutical composition, a more number of related substances may be produced.

The amount of the main drug component (a) is not particularly limited and any amount suffices as long as an amount effective as a medicament is contained. It is preferably 0.05-1.0 mg, more preferably 0.1-0.4 mg, as the amount of 2-amino-2-[2-(4-heptyloxy-3-trifluoromethylphenyl)ethyl]propane-1,3-diol.

The amount of the main drug component (a) is not particularly limited as long as an amount effective as a medicament is contained. It is preferably 0.05-1.0 mg, more preferably 0.1-0.4 mg, as the amount of 2-amino-2-[2-(4-heptyloxy-3-trifluoromethylphenyl)ethyl]propane-1,3-diol, with respect to 60 mg of the pharmaceutical composition, excluding the weight of a capsule when it is filled in the capsule. When the amount of the component (a) is small, particularly when it is less than 0.1 mg, many related substances may be produced.

As component (b) excipient used in the present invention, one or more excipients selected from dibasic calcium phosphate, calcium dihydrogen phosphate, dibasic sodium phosphate, and sodium dihydrogen phosphate can be mentioned.

In the present specification, the "dibasic calcium phosphate", "calcium dihydrogen phosphate", "dibasic sodium phosphate", and "sodium dihydrogen phosphate" are concepts including hydrates thereof and anhydrides thereof, unless particularly indicated.

The chemical formulas of excipients preferred as the component (b) excipient used in the present invention are shown below. Some of the component (b) excipients used in the present invention have other names, but the excipients having the same chemical formulas are encompassed in the present invention even when the names are different.

dibasic calcium phosphate hydrate: $CaHPO_4 \cdot n^1H_2O$ ($n^1$=0.5, 1, 1.5, 2)
anhydrous dibasic calcium phosphate: $CaHPO_4$ dibasic calcium phosphate: $CaHPO_4 \cdot 0\text{-}2H_2O$ calcium dihydrogen phosphate hydrate: $Ca(H_2PO_4)_2H_2O$ anhydrous calcium dihydrogen phosphate: $Ca(H_2PO_4)_2$ calcium dihydrogen phosphate: $Ca(H_2PO_4)_2 \cdot 0\text{-}1H_2O$ dibasic sodium phosphate hydrate: $Na_2HPO_4 \cdot n^2H_2O$ ($n^2$=1, 2, 5, 7, 8, 10, 12)
anhydrous dibasic sodium phosphate: $Na_2HPO_4$ dibasic sodium phosphate: $Na_2HPO_4 \cdot 0\text{-}12H_2O$ sodium dihydrogen phosphate hydrate: $NaH_2PO_4n^3H_2O$ ($n^3$=1, 2) anhydrous sodium dihydrogen phosphate: $NaH_2PO_4$ sodium dihydrogen phosphate: $NaH_2PO_4 \cdot 0\text{-}2H_2O$ That is, preferred excipients include dibasic calcium phosphate, calcium dihydrogen phosphate, dibasic sodium phosphate, and sodium dihydrogen phosphate. The excipient used in the present invention is further preferably dibasic calcium phosphate or calcium dihydrogen phosphate, particularly preferably dibasic calcium phosphate, most preferably anhydrous dibasic calcium phosphate.

The amount of the component (b) excipient is preferably 10 to 30 parts by weight with respect to 60 parts by weight of the pharmaceutical composition (when filled in a capsule, 60 parts by weight of the pharmaceutical composition excluding the weight of the capsule). When the amount of the component (b) is more than 30 parts by weight with respect to 60 parts by weight of the pharmaceutical composition, the dissolution rate tends to decrease, and when it is less than 10 parts by weight, the production of related substances tends to increase.

The amount of the component (b) excipient is not particularly limited. When it is filled in a capsule, the amount is preferably 10 to 30 mg with respect to 60 mg of the pharmaceutical composition excluding the weight of a capsule when it is filled in the capsule. When it is more than 30 mg, the dissolution rate tends to decrease, and when it is less than 10 mg, the production of related substances tends to increase.

The component (b') excipient used in the present invention is an excipient wherein a total peak area of related substances of the component (a) (that is, total value of the peak areas of the related substances) is less than 0.3%, preferably 0.28% or less, more preferably 0.25% or less, further preferably 0.23% or less, particularly preferably 0.2% or less, with respect to the total value of a peak area of the component (a) and the total peak area of the related substances of the component (a), in a peak area detected by HPLC of a mixture of the component (a) and the component (b') mixed such that a weight ratio thereof (component (a):component (b')) is 1:999 and stored open at 40° C., 75% RH for 4 weeks.

The above-mentioned peak area by HPLC can be measured according to the conditions described in the "Measurement method (A) of total amount of related substances" below.

The proportion (%) of the total peak area of the related substances of the component (a) to the total value of the peak area of the component (a) and the total peak area of the related substances of the component (a) can be calculated according to the "Calculation method (B) of total amount of related substances [%]" below.

Measurement Method (A) of Total Amount of Related Substances 10 ml of a diluent is put in a test tube containing a sample containing 1 mg of an amount of component (a) (mixture obtained by mixing component (a) and component (b') at a weight ratio (component (a):component (b')) of 1:999 and preserving the mixture), and the mixture is sufficiently dissolved and dispersed, followed by centrifugation. The supernatant is used as a sample solution and analyzed by the HPLC method under the following measurement conditions.

HPLC Measurement Conditions detection wavelength: 225 nm column: Ascentis (registered trade mark) Express C18, 4.6 mm×15 cm, 2.7 μm particle size, SUPELCO Co.

column temperature: 40° C.

injection volume: 50 μL mobile phase A: pH 2.8 sodium perchlorate buffer mobile phase B: acetonitrile flow: 1.0 mL/min gradient Program:

TABLE 1

| time [min] | % A | % B |
|---|---|---|
| 0-30 | 65 → 35 | 35 → 65 |
| 30-35 | 35 → 10 | 65 → 90 |
| 35-35.1 | 10 → 65 | 90 → 35 |
| 35.1-45 | 65 | 35 |

Calculation Method (B) of Total Amount of Related Substances [%]

Analysis is made by comparison of the HPLC chart (SC) of the sample (mixture of component (a) and component (b')), and the HPLC chart of additive (component (b')) alone and the HPLC chart (CC) of the standard solution (component (a)), and the total amount of related substances [%] is calculated by the following procedures.

Procedure 1. Based on the peak of an related substance different from that of component (a), and the peak considered to be of the same related substance from the retention time and peak shape, the difference in the peak area is determined by the following formula:

$$A_{SC}-A_{CC}=D$$

A: peak area

D: difference in peak area

Procedure 2. The total amount of related substances [%] (that is, proportion (%) of the total peak area of the related substances of the component (a) to the total value of the peak area of the component (a) and the total peak area of the related substances of the component (a)) is calculated by the following formula:

[numerical formula 1]

$$\text{total amount of related substances [\%]} = \frac{\sum_{k=1}^{n} D_k}{A_{SC}(\text{component) }(a)) + \sum_{k=1}^{n} D_k} \times 100$$

The component (b') excipient used in the present invention may be any pharmaceutically acceptable excipient. Examples thereof include dibasic calcium phosphate, calcium dihydrogen phosphate, dibasic sodium phosphate, sodium dihydrogen phosphate, calcium carbonate, calcium silicate, cornstarch, and the like, with preference given to the above-mentioned (b) excipient.

The component (c) sugar alcohol is, for example, mannitol or sorbitol, preferably mannitol. Mannitol may be either L form or D form, and D form, which is abundantly present in nature, is generally used.

When the amount of the component (c) sugar alcohol is more than 45 parts by weight with respect to 60 parts by weight of the pharmaceutical composition, the production of related substances tends to increase, and when it is less than 25 parts by weight, the dissolution rate of the main drug tends to decrease. Thus, it is, for example, 0 to 45 parts by weight, preferably 25 to 45 parts by weight, with respect to 60 parts by weight of the pharmaceutical composition (when filled in a capsule, 60 parts by weight of the pharmaceutical composition excluding the weight of the capsule).

The amount of the component (c) sugar alcohol is not particularly limited. When it is more than 45 mg, the production of related substances tends to increase, and when it is less than 25 mg, the dissolution rate of the main drug tends to decrease. When it is filled in a capsule, therefore, the amount is, for example, 0 to 45 mg, preferably 25 to 45 mg, with respect to 60 mg of the pharmaceutical composition excluding the weight of the capsule.

The weight ratio of the main drug component (a), and the total amount of the component (b) or component (b') excipient m and the component (c) sugar alcohol (component (a):total amount of component (b) or (b') and component (c)) is not particularly limited, and preferably 1:999 to 20:980, more preferably 1.5:998.5 to 8:992.

As regards the weight ratio of the component (b) or component (b') excipient and the component (c) sugar alcohol, not less than 10% of the component (b) or component (b') excipient may be contained from the aspect of the maintenance of stability. From the aspect of the maintenance of solubility, a preferred weight ratio (component (b) or (b'):component (c)) is 10:90 to 75:25, more preferably 25:75 to 50:50.

The pharmaceutical composition of the present invention is preferably a solid pharmaceutical composition.

The pharmaceutical composition of the present invention preferably further contains a lubricant.

The lubricant is not particularly limited and, for example, talc, magnesium stearate, calcium stearate, magnesium silicate, sucrose fatty acid ester (e.g., sucrose behenic acid ester, sucrose stearic acid ester), polyethylene glycol, stearic acid, light anhydrous silicic acid, hydrogenated oil (e.g., hydrogenated rapeseed oil, hydrogenated castor oil), glycerin fatty acid ester, sodium stearyl fumarate, and the like can be mentioned. Among these, talc, sucrose behenic acid ester, sucrose stearic acid ester, hydrogenated oil (hydrogenated castor oil type), and sodium stearyl fumarate are preferred, talc and sodium stearyl fumarate are more preferred, and talc is particularly preferred.

The pharmaceutical composition of the present invention may further contain additives such as disintegrant, binder, solubilizing agent, fluidizer, sweetener, foaming agent, surfactant, preservative, pH adjuster, colorant, flavor, excipients other than components (b) and (c), and the like.

The amount of the additive is not particularly limited and can be appropriately determined.

The dosage form of the pharmaceutical composition of the present invention is not particularly limited and is, for example, tablet form, capsule form, pill form, troche form, granule form, or powder form, and capsule form is preferred. As a capsule used for the capsule form, gelatin capsule, hydroxypropylmethylcellulose (HPMC) capsule, pullulan capsule, or the like can be mentioned. Among these, the pharmaceutical composition of the present invention is preferably filled in a gelatin capsule from the aspect of stability.

The pharmaceutical composition of the present invention can be produced by a known method generally used in the technical field of pharmaceutical preparations.

For example, the capsule preparation of the present invention can be produced by filling a capsule with a composition for filling a capsule which is prepared by mixing the main drug component (a), the component (b) or component (b') excipient, the component (c) sugar alcohol, and a lubricant.

As the above-mentioned composition for filling a capsule, a powder or granular composition for filling a capsule can be used.

For example, the capsule preparation included in the present invention can be produced by a production method including the following steps 1) to 6).

1) Component (b) or component (b') excipient is mixed with component (c) sugar alcohol as necessary by a blending machine to give the first mixture (excipient mixture).
2) The obtained first mixture is mixed with the main drug component (a) by a blending machine to give the second mixture.
3) The obtained second mixture is mixed with a lubricant as necessary by a blending machine to give the third mixture.
4) The obtained third mixture is sieved with a granulating machine to give the fourth mixture.
5) The obtained fourth mixture is mixed in a blending machine to give the fifth mixture (mixed powder for filling capsule).
6) The obtained fifth mixture is filled in a capsule by a capsule filling machine.

In the above-mentioned production method of the capsule preparation, the first mixture obtained in step 1) may be free of component (c) sugar alcohol, and component (b) or component (b') excipient may be contained in the first mixture.

In the above-mentioned production method of the capsule preparation, in an attempt to obtain a mixture, in which the main drug component (a) is uniformly dispersed, as the second mixture obtained in step 2), the operation of sieving by a granulating machine and mixing again by a blending machine may be repeated as necessary, after mixing the second mixture by a blending machine in step 2) and before step 3).

In the above-mentioned production method of the capsule preparation, the second mixture not containing a lubricant may become the third mixture obtained in step 3).

In the above-mentioned production method of the capsule preparation, in an attempt to obtain the fifth mixture optimal for filling a capsule, the operation of mixing again by a blending machine and sieving by a granulating machine may be repeated as necessary, after sieving the fourth mixture by a granulating machine in step 4) and before step 5).

In the above-mentioned production method of the capsule preparation, the capsule is not particularly limited. For example, a hard capsule may be used. Examples of the hard capsule include gelatin capsule, HPMC capsule, and pullulan capsule, with preference given to gelatin capsule.

The pharmaceutical composition of the present invention is useful for the treatment or prophylaxis of autoimmune diseases (e.g., rheumatoid arthritis, inflammatory bowel disease (ulcerative colitis, Crohn's disease, etc.), multiple sclerosis, encephalomyelitis, systemic lupus erythematosus, lupus nephritis, nephrotic syndrome, psoriasis, Type I diabetes mellitus, etc.); prophylaxis or suppression of resistance or acute rejection or chronic rejection against organ or tissue transplantation (e.g., transplantation of heart, kidney, liver, lung, bone marrow, cornea, pancreas, small intestine, the four limbs, muscle, nerve, fatty bone marrow, duodenum, skin, pancreatic islet cell and the like, including heterotransplantation) in mammals such as human, dog, cat, bovine, horse, swine, monkey, mouse and the like; graft vs host (GvH) disease due to bone marrow transplantation; and treatment or prophylaxis of allergic diseases (e.g., atopic dermatitis, allergic rhinitis, asthma, etc.).

EXAMPLE

While the present invention is further described in detail by way of the following Examples, they do not limit the present invention, and the invention may be changed without deviating from the scope of the present invention.

(I. Measurement Method (1) of Total Amount of Related Substances)

10 ml of a diluent was put in a test tube containing a sample containing 1 mg of an amount of 2-amino-2-[2-(4-heptyloxy-3-trifluoromethylphenyl)ethyl]propane-1,3-diol hydrochloride and the mixture was sufficiently dissolved and dispersed, followed by centrifugation. The supernatant was used as a sample solution and analyzed by the HPLC method under the following measurement conditions. The total amount of related substances was calculated based on the following calculation method.

HPLC Measurement Conditions detection wave length: 225 nm
column: Ascentis (registered trade mark) Express C18, 4.6 mm×15 cm, 2.7 μm particle size, SUPELCO Co.
column temperature: 40° C.
injection volume: 50 μL
mobile phase A: pH 2.8 sodium perchlorate buffer
mobile phase B: acetonitrile
flow: 1.0 mL/min gradient program:

TABLE 2

| time [min] | % A | % B |
|---|---|---|
| 0-30 | 65 → 35 | 35 → 65 |
| 30-35 | 35 → 10 | 65 → 90 |
| 35-35.1 | 10 → 65 | 90 → 35 |
| 35.1-45 | 65 | 35 |

Calculation Method of Total Amount of Related Substances [%]

Analysis was made by comparison of the HPLC chart (SC) of the sample, and the HPLC chart of additive alone and the HPLC chart (CC) of the standard solution, and the total amount of related substances [%] was calculated by the following procedures.

Procedure 1. Based on the peak of an related substance different from that of the main drug (2-amino-2-[2-(4-heptyloxy-3-trifluoromethylphenyl)ethyl]propane-1,3-diol hydrochloride), and the peak considered to be of the same related substance from the retention time and peak shape, the difference in the peak area was determined by the following formula:

$$A_{SC}-A_{CC}=D$$

A: peak area
D: difference in peak area

Procedure 2. The total amount of related substances [%] was calculated by the following formula:

[numerical formula 2]

$$\text{total amount of related substances [\%]} = \frac{\sum_{k=1}^{n} D_k}{A_{SC(main\ drug)} + \sum_{k=1}^{n} D_k} \times 100$$

(II. Measurement Method (2) of Amount of Related Substance)

A sample containing 1.1 mg of an amount of 2-amino-2-[2-(4-heptyloxy-3-trifluoromethylphenyl)ethyl]propane-1,3-diol hydrochloride was put in a 10 mL measuring flask, diluted with a diluent, sufficiently dissolved and dispersed, and filtered through a 0.45 μm membrane filter (PALL, Nylon Acrodisc (registered trade mark) 25 mm syringe filter). The first 2 mL was discarded, and the remaining solution was used as a sample solution. The solution was analyzed by the HPLC method under the same measurement conditions as in the aforementioned "Measurement method (1) of total amount of related substances" and the amount of related substance was calculated based on the following calculation method.

Calculation Method of Amount of Related Substance [%]

Using the peak area ($R_i$) of each related substance in the sample solution and the peak area ($R_m$) of the main drug (2-amino-2-[2-(4-heptyloxy-3-trifluoromethylphenyl)ethyl]propane-1,3-diol hydrochloride) in the sample solution, the amount of each related substance [%] was calculated by the following formula.

[numerical formula 3]

$$\text{amount of related substances [\%]} = \frac{R_i}{\sum(R_i) + R_m} \times 100$$

The total amount of related substances [%] was calculated by totaling the related substances of not less than 0.05%.

(III. Study of Excipients)

Reference Example 1

1 g of 2-Amino-2-[2-(4-heptyloxy-3-trifluoromethylphenyl)ethyl]propane-1,3-diol hydrochloride and 19 g of anhydrous dibasic calcium phosphate (Tomita Pharmaceutical Co., Ltd.) as an excipient were mixed by MECHANOMILL (OKADA SEIKO. CO., LTD.) at 800 rpm for 3 min and the mixed powder was passed through a sieve (aperture: 500 μm). 1 g was separated from the sieved product, mixed with 49 g of anhydrous dibasic calcium phosphate as an excipient by MECHANOMILL for 3 min, and then sieved again. The sieved mixed powder product was placed in a test tube by 1 g and stored under open conditions at 40° C., 75% RH for 4 weeks. After 4 weeks, the total amount of related substances was measured according to the above-mentioned "Measurement method (1) of total amount of related substances".

Reference Examples 2, 3, Comparison Reference Examples 1, 2

Using D-mannitol (Merck KGaA), D-sorbitol (Merck KGaA), lactose (DMV Fonterra Excipients), or crystalline cellulose (Asahi Kasei Chemicals Corporation) in place of anhydrous dibasic calcium phosphate as an excipient, a sieved mixed powder product was prepared in the same manner as in Reference Example 1 and the total amount of related substances was measured.

The above results are summarized in the following Table 3.

TABLE 3

| | excipient | total amount of related substances (%) |
|---|---|---|
| Reference Example 1 | anhydrous dibasic calcium phosphate | 0.2 |
| Reference Example 2 | D-mannitol | 0.3 |
| Reference Example 3 | D-sorbitol | 1.7 |
| Comparison Reference Example 1 | lactose | 6.5 |
| Comparison Reference Example 2 | crystalline cellulose | 2.0 |

Reference Example 4

0.138 g of 2-Amino-2-[2-(4-heptyloxy-3-trifluoromethylphenyl)ethyl]propane-1,3-diol hydrochloride and 53.862 g of dibasic calcium phosphate hydrate (Tomita Pharmaceutical Co., Ltd.) as an excipient were mixed by MECHANOMILL (OKADA SEIKO. CO., LTD.) at 800 rpm for 3 min, 6 g of talc sieved (22 mesh) previously was added thereto, and the mixture was further mixed for 1 min at 400 rpm by MECHANOMILL. The mixed powder was separated by 2 g each and stored at 40° C., 75% RH for 1 month under open conditions. One month later, the total amount of related substances was measured according to the above-mentioned "Measurement method (2) of amount of related substance".

Reference Example 5

Using anhydrous dibasic calcium phosphate (Merck KGaA) in place of dibasic calcium phosphate hydrate as an excipient, a mixed powder was prepared, and the total amount of related substances was measured in the same manner as in Reference Example 4.

The above results are summarized in the following Table 4.

TABLE 4

| | excipient | total amount of related substances (%) |
|---|---|---|
| Reference Example 4 | dibasic calcium phosphate hydrate | 0.11 |
| Reference Example 5 | anhydrous dibasic calcium phosphate | 0.13 |

(IV. Study of Lubricant)

Reference Examples 6 to 10

0.5 g of 2-Amino-2-[2-(4-heptyloxy-3-trifluoromethylphenyl)ethyl]propane-1,3-diol hydrochloride and 49.5 g of any lubricant in the following Table 5 were mixed by MECHANOMILL (OKADA SEIKO. CO., LTD.) at 800 rpm for 3 min, and the mixed powder was passed through a sieve (aperture: 500 μm). The sieved product was placed in a test tube by 100 mg and stored at 40° C., 75% RH under open conditions for 4 weeks or in a sealed state at 60° C. for 4 weeks. After 4 weeks, the total amount of related substances was measured according to the above-mentioned "Measurement method (1) of total amount of related substances".

The above results are summarized in the following Table 5.

TABLE 5

| | lubricant | manufacturer | total amount of related substances (%) 40° C. 75% RH | 60° C. |
|---|---|---|---|---|
| Reference Example 6 | talc | Merck KGaA | 0.1 | 0.6 |
| Reference Example 7 | sucrose behenic acid ester | Mitsubishi-Chemical Foods Corporation | not more than 0.1 | 0.2 |
| Reference Example 8 | sucrose stearic acid ester | Mitsubishi-Chemical Foods Corporation | 0.7 | 1.8 |
| Reference Example 9 | hydrogenated oil (hydrogenated castor oil type) | Freund Corporation/ Kawaken Fine Chemicals Co., Ltd. | not more than 0.1 | 0.2 |
| Reference Example 10 | sodium stearyl fumarate | JRS PHARMA | 0.1 | 0.2 |

(V. Study of Storage Stability of Capsule Preparation Containing Excipient and Lubricant in Combination)

Comparison Reference Example 3

0.345 g of 2-Amino-2-[2-(4-heptyloxy-3-trifluoromethylphenyl)ethyl]propane-1,3-diol hydrochloride and 134.655 g of D-mannitol (Merck KGaA) as an excipient were mixed by MECHANOMILL (OKADA SEIKO. CO., LTD.) at 800 rpm for 3 min and the mixed powder was sieved with FREWITT sizing and sieving machine (Freund Corporation, TC-LABO) under the conditions of aperture: 700 μm, rotating speed: 2500 rpm. The sieved product was divided into two parts by 54 g each, 6 g of talc (Merck KGaA) was added to each as a lubricant and mixed by MECHANOMILL (OKADA SEIKO. CO., LTD.) at 800 rpm for 3 min. The mixed powder was dispensed by 60 mg into a gelatin capsule. The obtained capsule was placed in a high-density polyethylene bottle and stored for 1 month at 40° C., 75% RH in a sealed state. Separately, the obtained capsules were placed in a glass bottle and stored for 1 month at 60° C. in a sealed state. The total amount of related substances at the start of storage and after storage was measured according to the above-mentioned "Measurement method (2) of amount of related substance".

Comparison Reference Example 4

Using sodium stearyl fumarate (JRS PHARMA) as an excipient in place of talc, a mixed powder was prepared, and the total amount of related substances was measured in the same manner as in Comparison Reference Example 3.

Reference Example 11

Using anhydrous dibasic calcium phosphate (Tomita Pharmaceutical Co., Ltd.) as an excipient in place of D-mannitol, a mixed powder was prepared, and the total amount of related substances was measured in the same manner as in Comparison Reference Example 3.

Reference Example 12

Using anhydrous dibasic calcium phosphate as an excipient in place of D-mannitol, a mixed powder was prepared, and the total amount of related substances was measured in the same manner as in Comparison Reference Example 4.

The above results are summarized in the following Table 6.

TABLE 6

D-mannitol-containing capsule

| | | total amount of related substances (%) | | | |
|---|---|---|---|---|---|
| | | 40° C. 75% RH | | 60° C. | |
| | lubricant | at start of storage | 1 month later | at start of storage | 1 month later |
| Comparison Reference Example 3 | talc | 0.14 | 0.88 | 0.14 | 2.3 |
| Comparison Reference Example 4 | sodium stearyl fumarate | 0.23 | 2.6 | 0.23 | 19.5 |

Anhydrous Dibasic Calcium Phosphate-Containing Capsule

| | | total amount of related substances (%) | | | |
|---|---|---|---|---|---|
| | | 40° C. 75% RH | | 60° C. | |
| | lubricant | at start of storage | 1 month later | at start of storage | 1 month later |
| Reference Example 11 | talc | 0.10 | 0.15 | 0.10 | 0.54 |
| Reference Example 12 | sodium stearyl fumarate | 0.10 | 0.20 | 0.10 | 2.0 |

When the D-mannitol-containing capsules (Comparative Reference Examples 3, 4) and the anhydrous dibasic calcium phosphate-containing capsules (Reference Examples 11, 12) using the same lubricant were compared, the total amount of related substances was remarkably small in the anhydrous dibasic calcium phosphate-containing capsules. When capsule preparations were formed, it was found that anhydrous dibasic calcium phosphate was clearly superior to D-mannitol in the storage stability, and can suppress the production of related substances.

When the D-mannitol-containing capsules (Comparative Reference Examples 3, 4) and the anhydrous dibasic calcium phosphate-containing capsules (Reference Examples 11, 12) using different lubricants were compared, the capsule preparations containing talc (Comparison Reference Example 3, Reference Example 11) showed remarkably smaller total amount of related substances than the capsule preparations containing sodium stearyl fumarate (Comparison Reference Example 4, Reference Example 12). When capsule preparations were formed, it was found that talc as a lubricant was clearly superior in the storage stability, and can suppress the production of related substances.

(VI. Study of Capsule)

Reference Example 13

0.345 g of 2-Amino-2-[2-(4-heptyloxy-3-trifluoromethylphenyl)ethyl]propane-1,3-diol hydrochloride and 134.655 g of D-mannitol (Merck KGaA) were mixed by MECHANOMILL (OKADA SEIKO. CO., LTD.) at 800 rpm for 3 min and the mixed powder was sieved with FREWITT sizing and sieving machine (Freund Corporation, TC-LABO) under the conditions of aperture: 700 μm, rotating speed: 2500 rpm. The sieved product was divided into two parts by 54 g each and mixed with 6 g of talc (Merck KGaA) by MECHANOMILL (OKADA SEIKO. CO., LTD.) at 800 rpm for 3 min. The mixed powder was dispensed by 60 mg into a gelatin capsule (Qualicaps Co., Ltd.) and a hydroxypropylmethylcellulose (HPMC) capsule (Qualicaps Co., Ltd.). The obtained capsule was placed in a high-density polyethylene bottle and stored for 1 month at 40° C., 75% RH in a sealed state. Separately, the obtained capsules were placed in a glass bottle and stored for 1 month at 60° C. in a sealed state. The total amount of related substances at the start of storage and after storage and the amount of individual related substance at a relative retention time (RRT) 1.19 when the retention time of the main drug was 1 were measured according to the above-mentioned “Measurement method (2) of amount of related substance”.

The above results are summarized in the following Tables 7 and 8.

TABLE 7

| | total amount of related substances (%) | | | |
|---|---|---|---|---|
| | 40° C. 75% RH | | 60° C. | |
| capsule | at start of storage | 3 months later | at start of storage | 1 month later |
| gelatin capsule | 0.14 | 1.1 | 0.14 | 2.3 |
| HPMC capsule | 0.14 | 2.6 | 0.07 | 3.7 |

TABLE 8

| | amount of individual related substance (%) at RRT = 1.19 | | | |
|---|---|---|---|---|
| | 40° C. 75% RH | | 60° C. | |
| capsule | at start of storage | 3 months later | at start of storage | 1 month later |
| gelatin capsule | 0 | 0.13 | 0 | 0.17 |
| HPMC capsule | 0 | 1.17 | 0 | 1.35 |

(VII. Measurement Method (3) of Amount of Related Substance)

The content of the capsule was taken out, a diluent (water (50%)-containing acetonitrile) was added to a concentration of 2-amino-2-[2-(4-heptyloxy-3-trifluoromethylphenyl)ethyl]propane-1,3-diol hydrochloride of 0.11 mg/mL, and the mixture was sufficiently dissolved and dispersed, and filtered through a 0.45 μm membrane filter (PALL, Ekicrodisc 25CR (registered trade mark) 25 mm syringe filter). The first 3 mL was discarded, and the remaining solution was used as a sample solution. The sample solution was diluted 1/100 with a diluent and used as the standard solution. The solution was analyzed by the HPLC method under the following measurement conditions, and the amount of related substance was calculated based on the following calculation method.

HPLC Measurement Conditions detection wavelength: 225 nm column: X-Bridge (registered trade mark) C18, 4.6 mm×75 mm, 2.5 μm particle size, Waters column temperature: 40° C.

injection volume: 50 μL mobile phase A: pH 2.8 sodium perchlorate buffer/acetonitrile mixed solution (9:1)

mobile phase B: acetonitrile/pH 2.8 sodium perchlorate buffer mixed solution (9:1)

flow: 1.5 mL/min gradient Program:

TABLE 9

| time [min] | % A | % B |
|---|---|---|
| 0-1 | 60 | 40 |
| 1-8 | 60 → 45 | 40 → 55 |
| 8-12 | 45 → 0 | 55 → 100 |
| 12-20 | 0 | 100 |

Calculation Method of Amount of Related Substance [%]

Using the peak area ($R_i$) of each related substance in the sample solution and the peak area ($R_{st}$) of the main drug (2-amino-2-[2-(4-heptyloxy-3-trifluoromethylphenyl)ethyl]propane-1,3-diol hydrochloride) in the standard solution, the amount of each related substance [%] was calculated by the following formula.

$$\text{amount of related substance [\%]} = R_i/R_{st} \quad \text{[numerical formula 4]}$$

The total amount of related substances [%] was calculated by totaling the related substances of not less than 0.1%.

(VIII. Stability Test of Solid Pharmaceutical Composition of the Present Invention (Gelatin Capsule Preparation))

Examples 1 to 3

The preparation of the present invention having the formulation shown in Table 10 below was produced by the following method.

D-mannitol (Merck KGaA) and anhydrous dibasic calcium phosphate (Merck KGaA) were mixed to give an excipient mixture. The aforementioned excipient mixture in an amount of about 3 times the weight of 2-amino-2-[2-(4-heptyloxy-3-trifluoromethylphenyl)ethyl]propane-1,3-diol hydrochloride was added to 2-amino-2-[2-(4-heptyloxy-3-trifluoromethylphenyl)ethyl]propane-1,3-diol hydrochloride and mixed. This mixture was added to the remaining excipient mixture obtained earlier, and talc (Merck KGaA) was further added and mixed. The mixed powder was sieved with a sizer. Thereafter, mixing with a blending machine, sieving with a sizer, and mixing with a blending machine were repeated. 60 mg of the obtained mixed powder was filled in a gelatin capsule by the capsule filling machine to give a capsule preparation of the solid pharmaceutical composition of the present invention. The obtained capsule preparation was divided into two, one was placed in a high-density polyethylene bottle, the other was packed with PTP (press through pack), and they were stored at 40° C., 75% RH for 6 months.

The total amounts of related substances at the start of storage and after storage for 6 months of the capsule preparations in respective forms are shown in the following Table 11. The total amount of related substances was measured according to the above-mentioned "Measurement method (3) of amount of related substance".

TABLE 10

| formulation | | | |
|---|---|---|---|
| | mass (mg/capsule) | | |
| component | Example 1 0.1 mg* | Example 2 0.2 mg* | Example 3 0.4 mg* |
| 2-amino-2-[2-(4-heptyloxy-3-trifluoromethylphenyl)ethyl]propane-1,3-diol hydrochloride | 0.11 | 0.22 | 0.44 |
| D-mannitol | 28.44 | 28.39 | 28.28 |
| anhydrous dibasic calcium phosphate | 28.45 | 28.39 | 28.28 |
| talc | 3.00 | 3.00 | 3.00 |
| total mixed powder | 60.0 | 60.0 | 60.0 |
| gelatin capsule | 1 capsule | 1 capsule | 1 capsule |

*indicated content as 2-amino-2-[2-(4-heptyloxy-3-trifluoromethylphenyl)ethyl]propane-1,3-diol

TABLE 11

| | | | total amount of related substances (%) 40° C. 75% RH | |
|---|---|---|---|---|
| | content | storage, package form | at start of storage | 6 months later |
| Example 1 | 0.1 mg | high-density polyethylene bottle | <0.10 | <0.10 |
| | | PTP | <0.10 | <0.10 |
| Example 2 | 0.2 mg | high-density polyethylene bottle | <0.10 | <0.10 |
| | | PTP | <0.10 | <0.10 |
| Example 3 | 0.4 mg | high-density polyethylene bottle | <0.10 | <0.10 |
| | | PTP | <0.10 | <0.10 |

In all the forms of Examples 1 to 3, the total amount of related substances after the storage test for 6 months was less than 0.10%, similar to that at the start of storage. From the above results, it is clear that the pharmaceutical composition of the present invention is superior in storage stability and can suppress production of related substances.

INDUSTRIAL APPLICABILITY

The pharmaceutical composition of the present invention is superior in storage stability and can suppress production of related substances. Therefore, it is useful in the field of medicament production.

This application is based on a patent application No. 2020-063606 filed in Japan, the contents of which are incorporated in full herein.

The invention claimed is:

1. A pharmaceutical composition comprising (a) 2-amino-2-[2-(4-heptyloxy-3-trifluoromethylphenyl)ethyl]propane-1,3-diol or a pharmaceutically acceptable salt thereof, (b) one or more excipients selected from dibasic calcium phosphate, calcium dihydrogen phosphate, dibasic sodium phosphate and sodium dihydrogen phosphate, and (c) sugar alcohol selected from mannitol and sorbitol.

2. The pharmaceutical composition according to claim 1, wherein the component (c) sugar alcohol is mannitol.

3. The pharmaceutical composition according to claim 1, wherein a weight ratio of the component (b) excipient and the component (c) sugar alcohol (component (b):component (c)) is 10:90 to 75:25.

4. The pharmaceutical composition according to claim 1, wherein the component (b) excipient is anhydrous dibasic calcium phosphate.

5. The pharmaceutical composition according to claim 1, further comprising talc.

6. The pharmaceutical composition according to claim 1, wherein the composition is filled in a gelatin capsule.

7. The pharmaceutical composition according to claim 1, wherein the component (a) 2-amino-2-[2-(4-heptyloxy-3-trifluoromethylphenyl)ethyl]propane-1,3-diol or a pharmaceutically acceptable salt thereof is 2-amino-2-[2-(4-heptyloxy-3-trifluoromethylphenyl)ethyl]propane-1,3-diol hydrochloride.

8. The pharmaceutical composition according to claim 1, wherein a weight ratio of the component (a) 2-amino-2-[2-(4-heptyloxy-3-trifluoromethylphenyl)ethyl]propane-1,3-diol or a pharmaceutically acceptable salt thereof and a total amount of the component (b) excipient and the component (c) sugar alcohol (component (a):total amount of component (b) and component (c)) is 1:999 to 20:980.

9. The pharmaceutical composition according to claim 1, wherein a content of the component (a) 2-amino-2-[2-(4-heptyloxy-3-trifluoromethylphenyl)ethyl]propane-1,3-diol or a pharmaceutically acceptable salt thereof is an amount of 2-amino-2-[2-(4-heptyloxy-3-trifluoromethylphenyl)ethyl]propane-1,3-diol, and is 0.1 to 0.4 mg with respect to 60 mg of the pharmaceutical composition excluding a weight of a capsule when the composition is filled in the capsule.

10. The pharmaceutical composition according to claim 1, wherein the pharmaceutical composition is a solid pharmaceutical composition.

11. A pharmaceutical composition comprising (a) 2-amino-2-[2-(4-heptyloxy-3-trifluoromethylphenyl)ethyl]propane-1,3-diol or a pharmaceutically acceptable salt thereof, and (b') excipient, wherein the component (b') excipient is an excipient wherein a total peak area of related substances of the component (a) is less than 0.3% with respect to the total value of a peak area of the component (a) and the total peak area of the related substances of the component (a), in a peak area detected by HPLC of a mixture of the component (a) and the component (b') mixed such that a weight ratio thereof (component (a):component (b')) is 1:999 and stored open at 40° C., 75% RH for 4 weeks.

12. The pharmaceutical composition according to claim 11, wherein the total peak area of the related substances of the component (a) is 0.2% or less with respect to the total value of the peak area of the component (a) and the total peak area of the related substances of the component (a).

13. The pharmaceutical composition according to claim 2, wherein a weight ratio of the component (b) excipient and the component (c) sugar alcohol (component (b):component (c)) is 10:90 to 75:25.

14. The pharmaceutical composition according to claim 6, which is filled in a gelatin capsule, wherein said capsule is stored in a polyethylene bottle.

15. The pharmaceutical composition according to claim 6, which is filled in a gelatin capsule, wherein said capsule is stored in a press through pack.

* * * * *